United States Patent
Collias et al.

(10) Patent No.: US 10,226,611 B1
(45) Date of Patent: Mar. 12, 2019

(54) GRIP LIGHT

(71) Applicant: Ushio America, Inc., Cypress, CA (US)

(72) Inventors: James H. Collias, Portland, OR (US); David Goldman, Portland, OR (US)

(73) Assignee: Ushio America, Inc., Cypress, CA (US)

( * ) Notice: Subject to any disclaimer, the term of this patent is extended or adjusted under 35 U.S.C. 154(b) by 0 days.

(21) Appl. No.: 15/978,089

(22) Filed: May 11, 2018

(51) Int. Cl.
| | |
|---|---|
| *A61M 37/00* | (2006.01) |
| *F21V 21/088* | (2006.01) |
| *F21W 131/403* | (2006.01) |
| *F21V 21/32* | (2006.01) |

(52) U.S. Cl.
CPC ..... *A61M 37/0076* (2013.01); *F21V 21/0885* (2013.01); *F21V 21/32* (2013.01); *F21W 2131/403* (2013.01)

(58) Field of Classification Search
CPC .............................................. A61M 37/0076
USPC ....................................................... 362/109
See application file for complete search history.

(56) References Cited

U.S. PATENT DOCUMENTS

| | | | | |
|---|---|---|---|---|
| 7,926,968 | B2* | 4/2011 | Liu | B43K 24/084 |
| | | | | 362/109 |
| 7,993,023 | B2* | 8/2011 | Wang | B25B 23/18 |
| | | | | 362/119 |
| 2005/0090851 | A1 | 4/2005 | Devlin | |
| 2005/0251152 | A1 | 11/2005 | Herweck et al. | |
| 2008/0089067 | A1 | 4/2008 | Grosjean | |
| 2014/0293590 | A1* | 10/2014 | Pathy | F21L 4/02 |
| | | | | 362/119 |
| 2018/0177992 | A1* | 6/2018 | Smith | A61M 37/0076 |

FOREIGN PATENT DOCUMENTS

KR          200470739 Y1    1/2014

OTHER PUBLICATIONS

KR200470739Y1, Tattooing machine with lighting means, English translation of Korean patent KR200470739Y1 granted on Jan. 8, 2014, from Google Patents, visited https://patents.google.com/patent/KR200470739Y1 on Feb. 21, 2018.

* cited by examiner

*Primary Examiner* — Christopher M Raabe
(74) *Attorney, Agent, or Firm* — J. Douglas Wells (57) ABSTRACT

A grip light for use with a tattoo machine having an exterior grip surface extending from an upper grip portion downward toward an opposite working end and surrounding a channel extending through the upper portion to the working end, light transmissive material running through the grip from a light receiving surface to a bottom surface of the working end, and a light pipe inlet for receiving light from a light pipe into the light receiving surface and thereby permitting light from the light pipe to be projected out from working end of the grip light to illuminate an area therebelow.

20 Claims, 8 Drawing Sheets

GRIP LIGHT

CROSS-REFERENCE TO RELATED APPLICATIONS

None.

BACKGROUND OF THE INVENTION

The technical field of the invention pertains generally to illuminating a work area and illuminating an area proximate to the working end of a handpiece, and, more particularly, to designs and methods for a tattooing lighting system and a tattoo machine grip that provides illumination from its working end to illuminate the area proximate to the tattoo tip and the tattoo artist's subject (i.e. the area being tattooed).

Generally, tattooing involves the mechanical placement of pigment into the skin's dermis, which is the second layer of skin/dermal tissue underlying the outermost layer of skin called the epidermis. The most common method of tattooing is via an electric tattoo machine, which pierces the epidermis to insert ink into the dermis using a single needle or a group of needles that are soldered onto a bar. The bar is then rapidly and repeatedly driven back and forth so that the needles pierce the skin typically between 50 and 100 times a second. The needles are typically single-use needles. The tattoo artist typically wears disposable garments such as a disposable plastic apron and eye protection, depending on the risk of contact with blood or other secretions. The tattoo artist typically wears nitrile or similar protective gloves. The subject area to be tattooed is washed prior to tattooing and is typically wiped frequently with a wet disposable towel during the process. All non-disposable equipment and supplies used are sterilized (such as in an autoclave) before and after each use.

Current tattoo lighting options include headlamps worn by the tattoo artist, tabletop light fixtures set alongside or near the artist, floor standing light fixtures positioned near the artist's work area, and soft box or other lighting devices more commonly used in film and photography. Each of these options provides particular benefits, yet none is ideal for tattooing. None of the available lighting options adequately address the problem of eliminating shadows cast upon the subject being tattooed.

Headlamps are cumbersome, uncomfortable, awkward, and typically cause the artist some distraction and disengagement from the subject to periodically adjust the headlamp with one or both hands. Headlamps cast shadows on the subject's skin, for example, wherever the tattoo artist's machine passes between the headlamp light source and the subject being tattooed. Tabletop and floor standing light fixtures likewise cause distraction and disengagement, with periodic adjustments needed to adequately illuminate the area being tattooed and avoid shadows. Soft box or umbrellas, or other lighting devices commonly used in photography, are sometimes used to provide even and diffused light. However, such lighting devices are typically large and cumbersome and also require periodic adjustments to illuminate the area desired. All of these lighting options require frequent repositioning of the light source or the artist's subject or the tattooist, or all three, to avoid shadows and adequately illuminate the area being tattooed.

U.S. patent application Ser. No. 11/974,869 filed Oct. 16, 2007 (pub. no. US 2008/0089067 A1) by Grosjean (hereinafter, "Grosjean") is hereby incorporated in its entirety by reference. Grosjean discloses a light attachable to and powered by a tattoo machine. The device consists of a gooseneck type attachment to a tattoo machine that is connected to the same electrical power connections used to power the tattoo machine. The neck portion extends from the top of the frame portion of the tattoo machine toward the tattoo grip and holds a light emitting diode (LED) light source at its end, with the light directable toward the tattoo tip. The gooseneck type device, however, does not provide a secure light source and is susceptible to vibration and unwanted movement due to the artist's hand movements. As the tattoo artist moves the machine back and forth to apply, for example, shading or lining, the gooseneck tends to wobble and sway, causing the light projected from the end of the gooseneck to move undesirably. The device needs to be periodically repositioned or reoriented with respect to the artist's subject to avoid unwanted shadows, is not easily coverable with disposable materials for each new subject, and likely requires cleaning between each new subject.

U.S. patent application Ser. No. 10/936,958 filed Sep. 9, 2004 (pub. no. US 2005/0090851 A1) by Devlin (hereinafter, "Devlin") is hereby incorporated in its entirety by reference. Devlin discloses a tattoo grip having light emitting diodes (LEDs) at the tip end of the grip and that are electrically powered, like Grosjean, via the electrical power connections used to power the tattoo machine. The device, however, is difficult to clean and limits the artist to the particular size of grip that includes the built-in LEDs. Another disadvantage of the Devlin device is its complexity of manufacture, and consequently higher cost, and increased weight by including LEDs and electrical wiring within the tattoo grip. Dissipating the heat generated by the LEDs is yet another problem with such device. Heat generated by the LEDs in the Devlin type device dissipates into the grip causing the grip to warm up during use.

Both the Grosjean and Devlin devices use fixed LEDs that likely provide poor light quality in terms of light color, intensity, and color rendering. Less expensive LEDs typically perform poorly in terms of color rendering, which is the ability of the LEDs to accurately/truthfully represent colors. Neither the Grosjean gooseneck type device nor the Devlin type device allow for cost effective use of higher quality light sources. Standard incandescent light sources render colors very well and typically provide warmer/yellow light with a color temperature of around 2500 Kelvin. By comparison, fluorescent lighting typically provide light with a cool white appearance and color temperature around 5000 Kelvin. Generally, standard fluorescent and lower cost LED lights do not render colors as well as standard incandescent lights.

What is needed, therefore, are new designs and methods for illuminating an area proximate to the working end of a handpiece or tattoo machine grip that address shortcomings of the available designs and methods.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

For a more complete understanding of the present invention, the drawings herein illustrate examples of the invention. The drawings, however, do not limit the scope of the invention. Similar references in the drawings indicate similar elements.

DESCRIPTION OF PREFERRED EMBODIMENTS

In the following detailed description, numerous specific details are set forth in order to provide a thorough understanding of the preferred embodiments. However, those skilled in the art will understand that the present invention may be practiced without these specific details, that the present invention is not limited to the depicted embodiments, and that the present invention may be practiced in a variety of alternate embodiments. In other instances, well known methods, procedures, components, and systems have not been described in detail.

Although preferred embodiments are presented and described in the context of a tattooing lighting system comprising a light source box, a light guide, a work area light, and a tattoo machine grip that provides illumination from its working end to illuminate the area proximate to the tattoo tip and the area being tattooed, numerous separable inventive aspects are presented that may be used in a variety of other lighting applications and with the use of a variety of other types equipment associated with various lighting applications. For example, the structures and methods discovered and disclosed herein for inserting a light guide (or light pipe, or fiber optic bundle, or fiber optic cable) into a tattoo grip having a light transmissive region therewithin adapted to receive light from the light guide and project the received light outward through a working end, or tattoo tip end, of the tattoo grip, preferably in a ring or annular shaped pattern for 360 degree illumination about the tattoo tip, thereby providing improved lighting near the tattoo tip and area being tattooed, may also be used more generally to illuminating an area proximate to the working end of a handpiece. The handpiece may comprise, for example, a dental appliance or other structured handheld tool having a grip portion through which light is received from a light guide, transmitted through a transmissive region within the radial interior of the handpiece, and projected (ideally in a 360 degree unobstructed ring or annular shape about an operative center portion) outward from the working end of the handpiece.

The present inventor(s) discovered new, unique, and truly innovative methods, systems, and apparatus for improving lighting used with tattoo machines and in the art of tattooing.

Various embodiments are illustrated and described in the figures, sketches, details, descriptive materials, and pictures submitted herewith. The various embodiments include separable inventive aspects which are separately patentable. The listed inventive aspects are not exhaustive or comprehensive, and further/additional separable inventive aspects are included in the submitted materials but may not be specifically or particularly identified or described in words due to the need to capture (in many instances in detailed illustrations, pictures, or sketches) the many separable inventive aspects in this disclosure.

Figure 1:
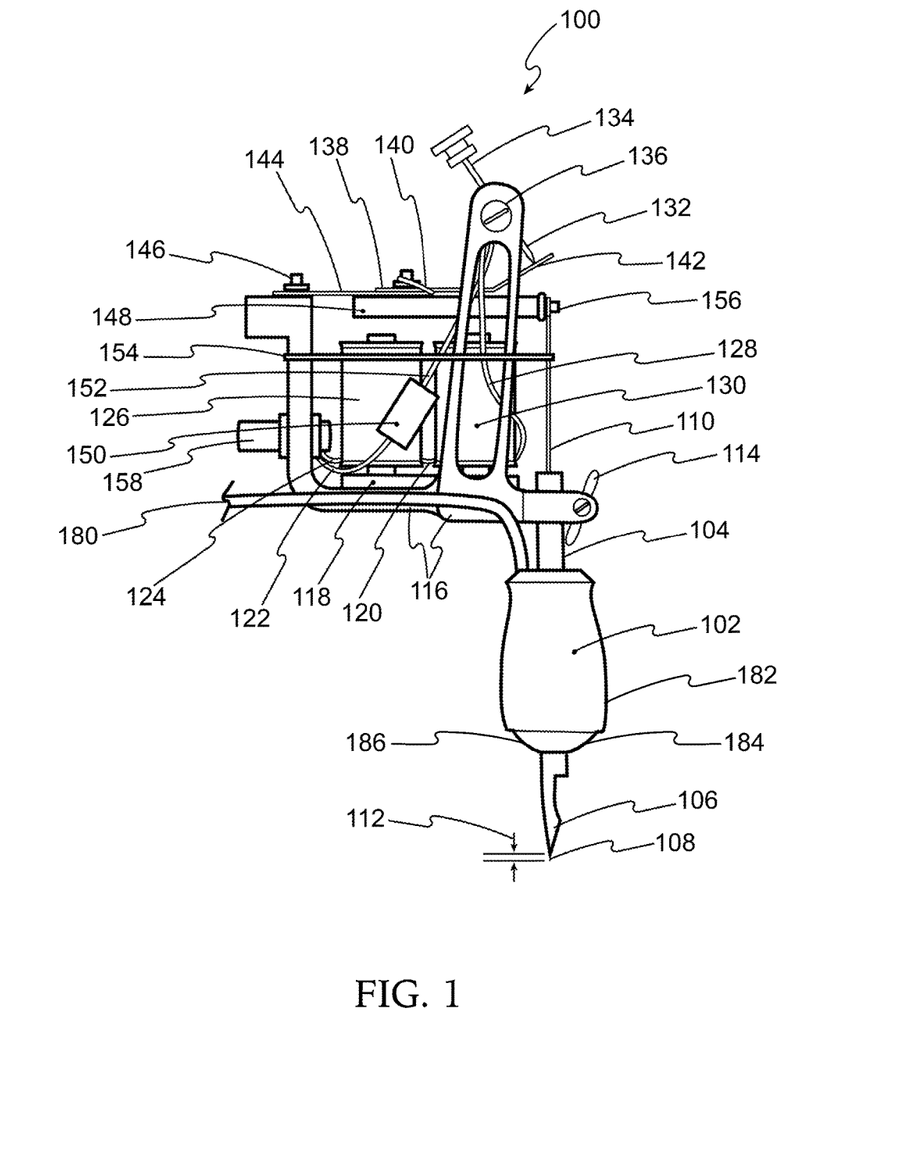
FIG. 1 is a side view of a coil type tattoo machine with an illuminated grip (or grip light), according to preferred embodiments.

The illustration in FIG. 1 is side view of a coil type tattoo machine 100 with an illuminated grip (or grip light) 102, according to preferred embodiments. Most coil type tattoo machines operate similar to the coil type tattoo machine 100 shown in FIG. 1, and most comprise similar components, except the tattoo machine 100 incorporates a novel and non-obvious improvement in its grip (or barrel) 102. The grip 102 preferably comprises means for receiving a light guide or light pipe 180, whereby light is received into a light transmissive region in the grip 102 and projected from the working end of the grip 102, such as from one or both surfaces 184, 186. Preferably, light is projected from surfaces 184, 186 (and more preferably a ring-shaped or annular surface comprising 184, 186 encircling tattoo tip 106) so as to illuminate a working area where a tattoo is being applied and proximate to the point (tip end of the tattoo needle) 108 protruding from the tattoo tip 106 that extends from the working end of grip 102 and guides the needle tip 108.

In preferred embodiments, the light pipe 180 extends from the non-working end of the grip 102 and may be easily pulled from and re-inserted into the grip 102. The light pipe 180, when inserted in the grip 102, preferably extends toward the lower portion or bottom of the tattoo machine frame 116, and outward toward the rear of the tattoo machine 100, preferably in the same general direction away from the tattoo machine as a power clipcord or power cable connected to the negative electrical power terminal 146 and positive electrical power terminal 158. In other embodiments, the light pipe 180 may be fed through a clip (not shown) or other structure comprising the frame 116 or other structure.

Extending away from the grip 102 and opposite the tattoo tip 106, as shown, is the tube 104, which is securely captured within the tube clamp or vice 114 attached to the lower frame 116 of the tattoo machine. The needlebar 110 extends downward through the tube 104 and, as it is moved upward and downward, causes up and down movement of the needle point 108 and change in the length of needle 112 protruding from the end of the tattoo tip 106. The amount or distance of longitudinal travel upward and downward is controlled by the longitudinal displacement or travel of the armature bar 148 where (shown in FIG. 1) a top hat style nipple 156 holds the eye of the needlebar 110. Different methods of holding the eye of the needlebar 110 to the end of the armature bar 148 are used. For example, a grommet may be used to secure the eye. One or more rubber bands 154 are commonly used to further secure the needlebar 110 to the armature bar 148, to soften or dampen the longitudinal movement of the needlebar 110, and/or, in some embodiments (particularly in embodiments where the needlebar 110 extends as a unitary component downward through the tube 104, grip 102, tattoo tip 106, and ending at the point or tip end 108 of needle), to urge the needlebar 110 toward one side (i.e. the closed or non-windowed side, as shown in FIG. 1) of the tattoo tip 106.

Tattoo artists frequently build their own tattoo machines to accommodate personal preferences and to address various needs in tattooing. The artist may prefer, for example, a grip 102 having a larger or smaller diameter, or shape other than substantially cylindrical, or a grip that is longitudinally longer or shorter, or a grip 102 having unique colors or designs for its exterior surface 182. Tattoo grip tape (not shown) is often applied over the exterior surface 182, to provide extra cushioning and/or grip/slip resistance, or to bulk up the overall grip.

The tattoo artist may select different combinations of tube, grip, tip, and needle/needlebar. Each may be separately selected by the artist. Or the artist may choose to use a single-piece tube-grip-tip or tube-grip or grip-tip assembly. The components or assemblies may be autoclavable or disposable. The needle is preferably disposable. However, tattooists may fabricate their own needles or each needlebar-needles assembly by soldering needles to the end of each needlebar.

Tattoo artists also frequently build, modify, repair, rebuild, and perform regular maintenance to their machines. A typical coil type tattoo machine comprises a frame 116 as shown in FIG. 1. A yoke 118 is set on the lower portion of the frame 116, upon which a rear coil bobbin 126 and front coil bobbin 130 are positioned. An electrical wire 124 connects the rear binding post (positive power terminal) 158 with wire winding in the rear coil 126. Wire winding in the rear coil 126 connects with wire winding in the front coil 130 via a wire 120, and wire from the front coil 130 connects to the front binding post 136 via a wire 128. A capacitor 150 is typically interconnected between the rear binding post 124 and front binding post 136 via wires 122, 152 as shown. The armature bar 148 is suspended from a rear portion of the frame by a rear spring 144 attached at the negative power terminal 146. A front spring 138 extends forward from the rear spring 144 to an end 142 that is oriented so as to make electrical contact with a contact screw 134 when the armature bar 148 is in an un-energized position (as shown in FIG. 1).

Generally, when electrical power is provided to the terminals 158, 146 electricity flows from the positive terminal 158 through the rear coil 126, the front coil 130, contact screw 134, front spring 138, and rear spring 144 to the negative terminal 146. The electricity flowing through the coils causes the coils to act as magnets to pull the armature bar 148 downward, thereby pulling the end 142 of the front spring 138 downward away from the end 132 of the contact screw, and de-energizing the coils. When the coils are de-energized they no longer act as magnets, so the armature bar 148 springs back to its upward position whereafter the end 132 of the contact screw touches the end 142 of the front spring 138, thereby re-energizing the coils and causing the coils to again act as magnets to pull the armature bar 148 downward. This process repeats at rates between 50 and 100 Hertz. An o-ring 140 is routinely used at the base of the front spring 138 to soften and dampen the up and down longitudinal movement of the armature bar 148.

Tattooists frequently modify their tattoo machines by replacing or readjusting/repositioning coils, changing the capacitor 150 to different capacitance values, repositioning an o-ring 140 under the front spring 138, and/or adding one or more rubber band 154, to achieve a desired speed, distance of needlebar longitudinal travel, impact force between armature bar and coils and/or contact screw and front spring, or to reduce machine noise.

The tattoo artist's work area or bench space is typically highly individualized according to preferences and choices regarding the use of disposable versus autoclavable tube-grip-tip and needlebar-needle combinations. The artist's work area typically comprises a table or bench for holding tattoo machines, tattoo needles, tubes and grips, ink caps and rinse cups, alcohol and soap/cleansers, protective gloves and garments, towels, stencils, other supplies, and lighting. The present inventor(s) discovered and determined that while every tattoo artist's bench is different, they have similar elements. Multiple machines or tips are needed, everything needs to be sterile, and the artists need to see what they are working on. Space can be limited, autoclaves may be inaccessible, and the artist may need their station to be mobile. The lighting needs to work in different situations.

Figure 2:
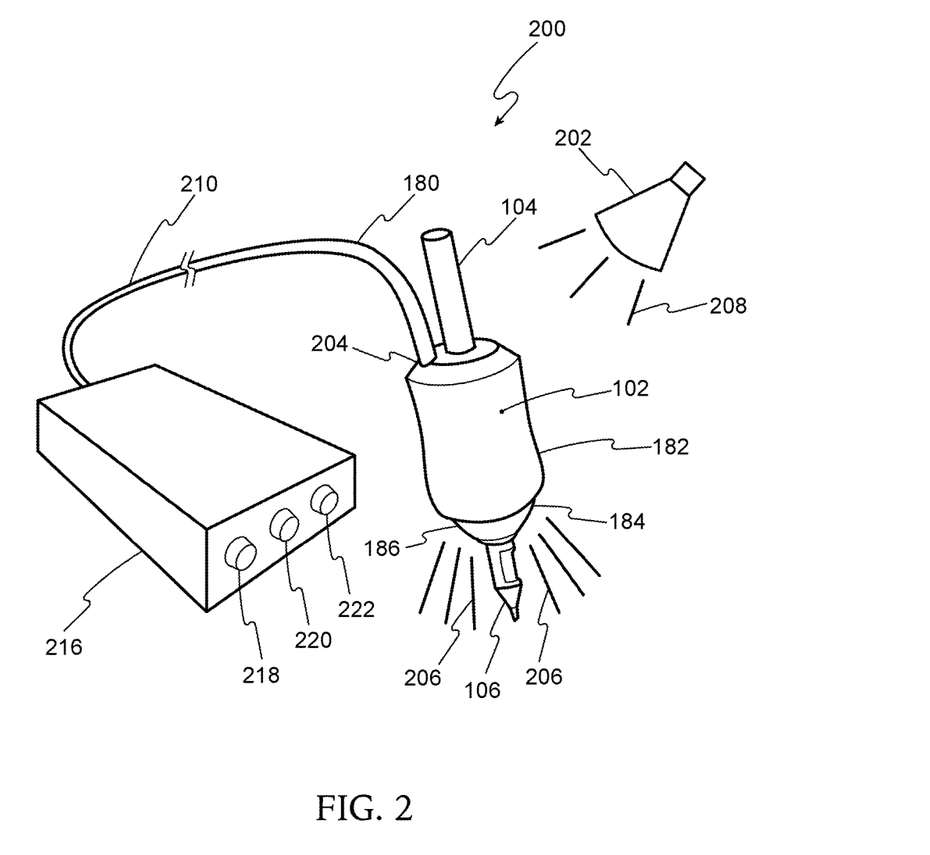
FIG. 2 is a perspective view of a grip light system, according to preferred embodiments.

The present inventor(s) discovered and invented new methods and devices to address the shortcomings of available lighting. A perspective view of a grip light system 200, according to preferred embodiments, is illustrated in FIG. 2, which includes a grip light 102, light pipe 180, light source box 216, and, preferably, a wirelessly controlled area light 202. As previously shown and described, the grip light 102 preferably comprises a handheld sized, generally cylindrically shaped exterior grip portion/grip surface 182 (although shapes other than cylindrical may be used); and means for receiving a light guide or light pipe 180, whereby light is received into a light transmissive region in the grip 102 and projected from the working end of the grip 102, such as from surfaces 184, 186. In preferred embodiments, an end of the light pipe 180 may be fed into an opening 204 in the grip 102 end opposite the tattoo tip 106 so that the light pipe 180 extends away from the grip 102, preferably in a direction substantially parallel to the tube 104. With the light pipe 180 inserted to enable light transmission through the light transmissive region in the grip 102, and with light projected through the light pipe 180, light shines out 206 of the bottom surfaces 184, 186 in the area proximate to and around the tattoo tip 106 and the area being tattooed (thereunder).

The present inventor(s) discovered and determined the light projected from the grip light 102 is not susceptible to vibration or unwanted movement. The light from the grip light 102 is always directed to where the tattooist points the grip and tattoo tip, i.e. toward the area being tattooed. The tattooist does not have to disengage from their work on the tattoo to reposition lighting or readjust the subject being tattooed to avoid shadows. The grip light 102, the present inventor(s) discovered, eliminates shadows at the work site and solves the problem of shadows cast upon the subject's skin being tattooed.

Sanitation is improved. The grip light 102 may comprise disposable or autoclavable materials. For example, the tube 104, grip 102, and tip 106 may be disposable and discarded after use, or may comprise autoclavable materials if the tattooist prefers. A tattooist may, for example, prefer to use a particularly shaped autoclavable tube-grip-tip combination for lining and single color work, and disposable tube-grip-needle cartridge setups for shading and multiple color tattoo work. A similar type of protective slip cover used for tattoo machine clipcords may be used for the portion of the light pipe 180 inserted into the grip 102.

Light quality and controllability is improved. The present inventor(s) discovered and determined higher quality lighting components may be used in a remote light engine or light source, with additional capabilities to control color and intensity. As shown in FIG. 2, the light pipe 180 extends outward to a portion of the light pipe 210 leading from a light source box 216 that comprises a light source and adjustments 218, 220, 222 for controlling color temperature/color mixing, brightness/intensity, and/or other characteristics of light introduced from the light source box 216 and received by the light pipe 210 and supplied to the grip light 102 via the light pipe 180.

Complexity is reduced, weight is reduced, and costs are reduced. The present inventor(s) discovered and determined that by providing light to the grip light 102 via a light pipe 180 reduces the manufacturing complexity, weight, and costs of the grip light 102. The grip light 102 preferably comprises light transmissive material formed to receive light from a light pipe 180 and project the transmitted light from the working end of the grip light 102. Instead of fitting all of the electrical wiring, heat sinks, and LEDs or other light source into the grip, the grip 102 comprises a lightweight, very simple grip with light transmissive material; and the light source, heat sinks, electrical wiring, and other structure required for the light generating means are preferably remotely located in the light source box 216. The present inventor(s) discovered and determined that the grip light 102, with the light source and light generating means remotely located, may be manufactured at much lower cost and comprise a lighter weight and smaller dimensional sizes.

In preferred embodiments, an area light 202 is used to illuminate the tattooists bench area and/or supplement illumination of the tattooists subject and work area. Preferably the light shining 208 from the area light 202 is wirelessly controlled to allow for greater flexibility in its use, coordination with use and control of the grip light 102 and light shining 206 therefrom, and/or reducing wiring and clutter within and around the tattooist's workspace. In some embodiments, the area light 202 may be wirelessly controlled using circuitry incorporated into the light source box 216. In some embodiments the area light 202 is controlled via wired connection to and controls within the light source box 216.

The grip light 102, as shown in FIG. 2, may comprise various combinations. In preferred embodiments, the grip light 102 comprises the previously described substantially cylindrically shaped device having a grip surface 182, that receives a light pipe 180 and a tube 104 at an upward or non-working end, and that receives a tattoo tip 106 at a lower or working end. No extra electrical connections to the tattoo machine power terminals 146, 158 are required. And no wiring or electrical components are needed in the grip 102 itself. The grip 102 is preferably inexpensively manufactured and disposable, intended for single use and replacement for subsequent clients. And the tube 104 and tattoo tip 106 preferably comprise disposable components that are likewise used for a particular client and then replaced for the next subsequent client. Preferably, tattoo tips 106 may be swapped out during use so that the tattooist is able to use different tattoo tips 106 (for different needle arrangements, or color choices, etc.) and use the same grip 102 while working on a particular tattoo and client.

However, in some embodiments, the grip 102 may incorporate an integral tube 104, or an integral tattoo tip 106, or both. In preferred embodiments, the tube 104, grip 102, and tattoo tip 106, whether as a single integrated unit (integral tube-grip-tip) or in two (integral tube-grip or integral grip-tip) or three units (separate tube, grip, and tip), are disposable and intended for single use. In some embodiments, a disposable grip 102 may be used with a non-disposable, autoclavable tube 104 and/or a non-disposable, autoclavable tattoo tip 106. In still other embodiments, the grip light 102 may be non-disposable or may comprise a one-piece non-disposable grip having an integral tube 104 and tattoo tip 106, using materials that may be subjected to sterilization or autoclaving.

Figure 3:
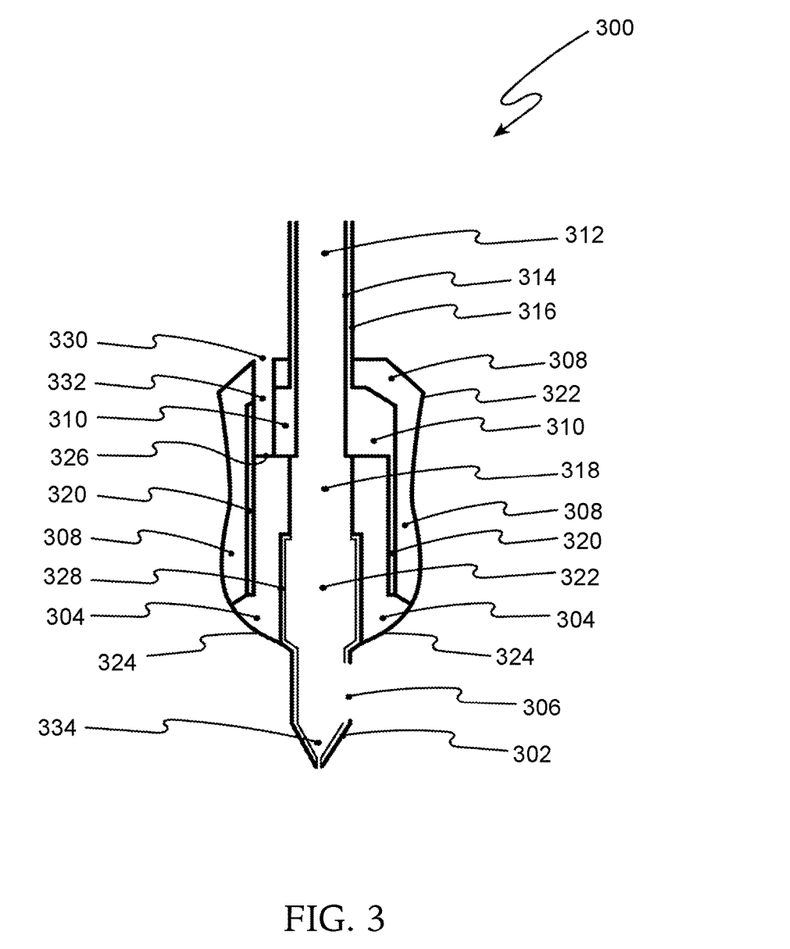
FIG. 3 is a cross-sectional view of the grip light shown in FIG. 2, according to preferred embodiments.

FIG. 3 provides a cross-sectional view 300 of the grip light 102, tube 104, and tip 106 shown in FIG. 2, according to preferred embodiments. As shown, the grip light 102 comprises an exterior grip surface 308 surrounding structural inner material 310 formed to capture light transmissive material 304 within the grip, with the light transmissive material 304 extending downward from a light receiving surface 326 to bottom surfaces 324 that form the bottom or working end of the grip. In preferred embodiments, the end of a light pipe 180 may be inserted into an opening 330 formed in the upper portion of the exterior grip surface 308 and fed downward into an opening 332 formed within the inner material 310 until the end of the light pipe 180 stops against the light receiving surface 326. Light received from the light pipe 180 is transmitted through the transmissive material 304 and projected out from the bottom surfaces 324 of the working end of the grip. The transmissive material 304 preferably comprises clear optic material. The bottom surfaces 324 preferably extend 360 degrees around the tattoo tip 302.

The inner material 310 is shown in FIG. 3 as having a thicker dimension above the light transmissive material 304 and a thinner dimension in a region 320 between the exterior surface material 308 and the light transmissive material 304. The inner material 310 is also shown extending upward to form a tube 104 with an inner surface 314, an outer surface 316, and hollow interior space 312. The open or hollow interior space 312 of the tube 104 extends longitudinally downward through an opening 318 extending through the light transmissive material 304, further downward through open spaces 322 and 334, the resulting opening (or longitudinal channel) 312, 318, 322, 334 sized to allow insertion of a tattoo needle and needlebar from the upward open end of the tube 104 and downward to the open end of the tattoo tip 302.

The exemplary cross-section shown in FIG. 3 illustrates a grip light 102 having an integral tube 104 and integral tattoo tip 302 (or tattoo tip 106), according to some embodiments. In some embodiments, the tube 104 may comprise a separate component insertable into, for example, a hole in the top of the grip and inner material 310 that is sized to receive and retain the inserted tube. In some embodiments, the grip light 102 includes the tube 104 as a component comprising a longitudinal hole/opening/channel 312 and material thickness 314-316 that is incorporated into a disposable tube-grip combination. In preferred embodiments, the grip light 102 incorporates a tube 104 and provides for the use of replaceable tattoo tip cartridges or needle cartridges that insert into the lower or working end of the grip light 102 and into a cartridge receiving portion 328. Tip and needle cartridges, as will be described and illustrated in FIGS. 4 and 5, have various structures and associated components. Preferably, the grip light 102 incorporates features as described and shown in FIG. 3 such that replaceable tip or needle cartridges may be used.

Although not shown, in other embodiments the grip light 102 may comprise exterior surface material 308 and light transmissive material 304 substantially as shown in FIG. 3 and described above, with inner material 310 sized and oriented to receive what is referred to as a full tube, wherein the full tube comprises a tube 104 that extends downward all of the way through the grip barrel and that integrally includes the tattoo tip 106. A grip light 102 configured to be used with a full tube, would preferably resemble, with the full tube removed, the grip 102 illustrated in FIG. 2 with the tube 104 and tip 106 removed.

Generally, different replaceable tip and needle cartridges are commercially available each of which provide a needle guide (i.e. tip end) having a particular shape to accommodate particular groupings and shapes of needles. For example, needles are available in a number of profiles such as diamond, round, flat, and magnum. The round profile, for example, includes a number of needles arranged in a round circle. The flat profile includes a number of needles arranged in a single row. Magnum needles incorporate two rows of needles. The needles are typically bonded or soldered to the end of the needlebar opposite the needlebar eye in the case of full needlbar/needles, or bonded to the end of a bar in the case of a needle cartridge.

Figure 4:
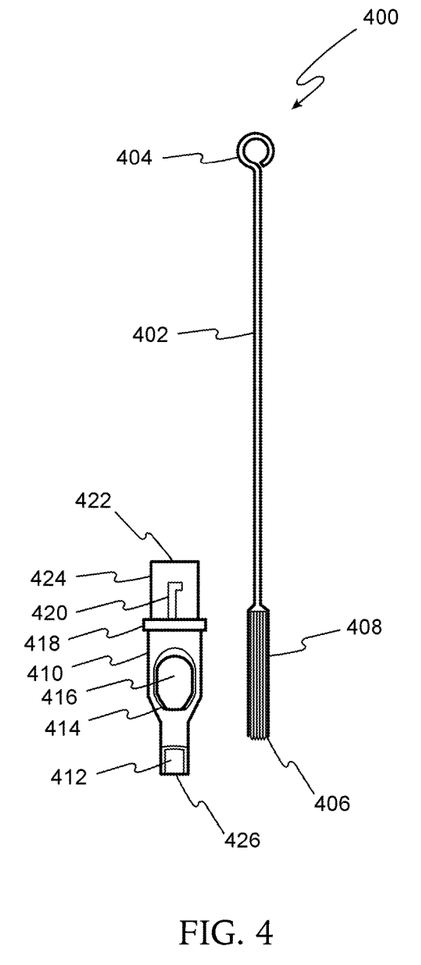
FIG. 4 is a top view of a tattoo needle and receiving tattoo tip, according to preferred embodiments.

FIG. 4 is a top view 400 of a tattoo needle 402 and receiving tattoo tip 410, according to preferred embodiments. The tattoo needle 402 comprises an eye 404 that attaches to the armature bar 148 of a coil type tattoo machine, a mid-section or bar portion extending from the eye 404, and the needles 408 bonded or soldered to the end opposite the eye 404. The numeral reference 402 is shown pointing to the mid-section or bar portion and is also referred to as the needlebar. The needles 408 are shown in a flat profile, with several needle points 406 arranged in a line. The needle 402 is the type of needle/needlebar used with a full tube setup or a setup using a replaceable tattoo tip/tip cartridge 410. In preferred embodiments, the needle 402 is inserted into the open end of tube 104 and fed downward through the longitudinal channel within the grip light 102 such that the needles 408 are positioned within the tattoo tip guide 412.

The tattoo tip or tip cartridge 410 comprises a tip end 426 from which the needle points 406 extend for piercing the skin during tattooing, an open guide portion 412 which guides the needles 408, a cutout 414 through which the tattooist may observe ink flow and needle movement, and an open back end 422 opposite the tip end 426 through which the needles 408 are inserted. The cutout 414 creates a window area/opening 416 which corresponds to the opening 306 illustrated in the cross-sectional view in FIG. 3. The back portion 424 of the cartridge preferably inserts into the working end of the grip light 102 until reaching the ridge 418, whereafter the cartridge may be twisted to engage molded-in locking material 420.

Figure 5:
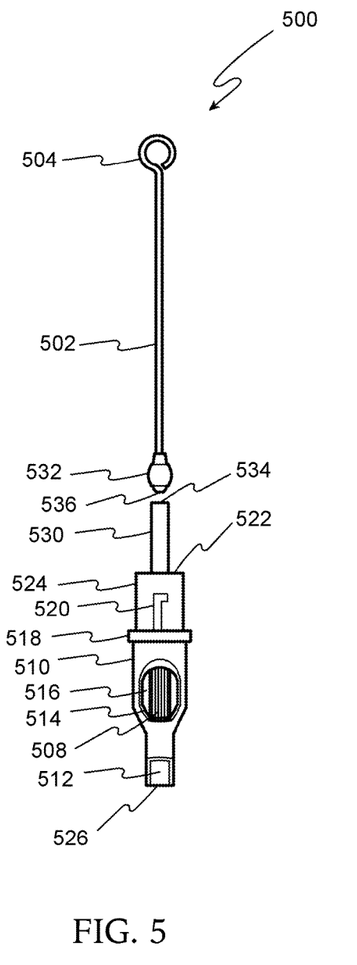
FIG. 5 is a top view of a tattoo needle cartridge and plunger bar, according to preferred embodiments.

FIG. 5 is a top view 500 of a tattoo needle cartridge 510 and plunger bar 502, according to preferred embodiments. The plunge bar 502 comprises an eye 504, middle section or bar section (pointed to by reference numeral 502), and a plunger 532. In preferred embodiments, the plunger bar 502 is inserted plunger 532 first into the tube 104, and the tattoo tip 106 (as shown in FIG. 2) comprises a needle cartridge 510. With the plunger bar 502 inserted into the tube 104, the plunger surface 536 contacts and pushes against the end 534 of the needle cartridge bar 530, which is connected to a spring within the cartridge 510 so that the needles 508 move back and forth (up and down) within the cartridge.

The tattoo tip or tip cartridge 510 comprises a tip end 526 from which the needle points extend for piercing the skin during tattooing, an open guide portion 512 which guides the needles 508, a cutout 514 through which the tattooist may observe ink flow and needle movement, and an open back end 522 opposite the tip end 526 through which the needle cartridge bar 530 protrudes/extends. The cutout 514 creates a window area/opening 516 which corresponds to the opening 306 illustrated in the cross-sectional view in FIG. 3. The back portion 524 of the cartridge preferably inserts into the working end of the grip light 102 until reaching the ridge 518, whereafter the cartridge may be twisted to engage molded-in locking material 520.

Figure 6:
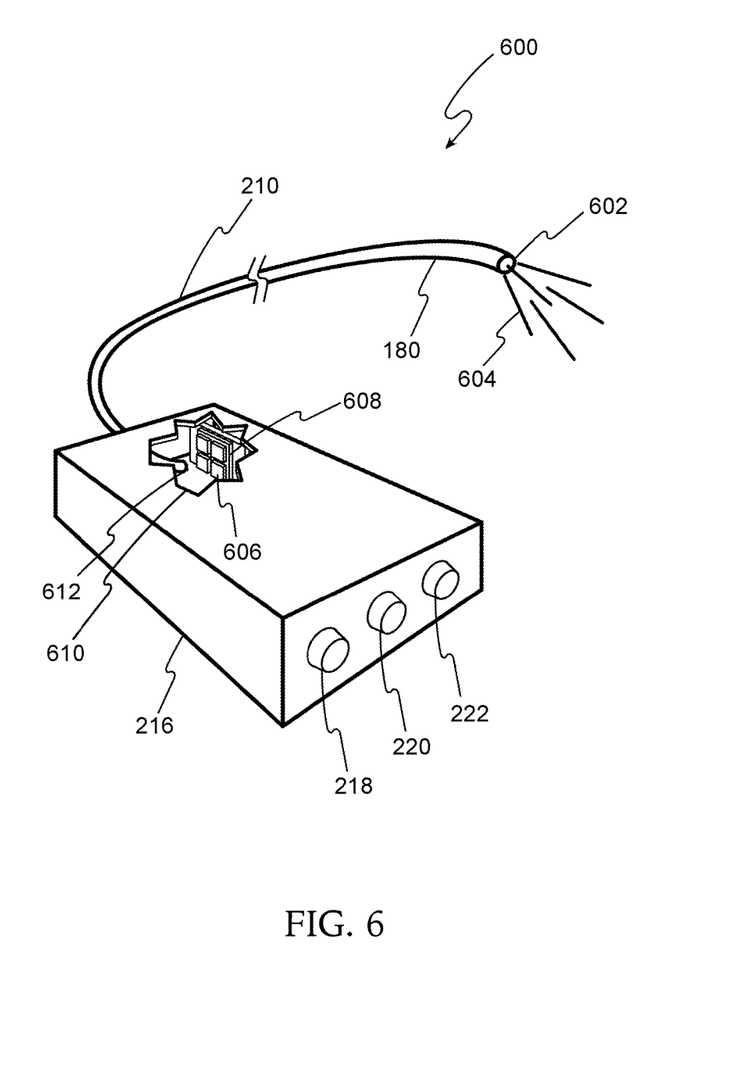
FIG. 6 is a perspective cutaway view of the light source box shown in FIG. 2, according to preferred embodiments.

Turning now to providing light to the light pipe 180, FIG. 6 provides a perspective cutaway view 600 of the light source box 216 shown in FIG. 2, according to preferred embodiments. The light pipe 180 may comprise a light guide or fiber optic bundle or fiber optic cable or optic fiber capable of projecting/shining 604 light from an end 602 insertable into an opening 204 of a grip light 102. The light pipe 180 extends to a portion of the light pipe 210 leading from a light source box 216. The light pipe 180 portion extending from the end 602 is preferably coverable by a disposable protective cover, similar to the disposable materials used for covering a tattoo machine clipcord. Alternatively, the light pipe 180 may be wiped clean with typically used sanitizers, or made inexpensively enough to be disposable.

In preferred embodiments, as shown in the cutout 610, a light source 606 is provided in the light source box 216 which generates and injects light into a receiving end 612 of the light pipe 210, 180. The light source 606 is preferably coupled with a small internal heat sink or other cooling means within the light source box 216. The present inventor(s) discovered and determined that the grip 102 remains cool during operation due to dissipation of heat generated by the light source within the light source box 216. Heat from the light source 606 is preferably dissipated and managed within the light source box 216 rather than in the grip 102.

Preferably the light source 606 is capable of generating high quality light with controllable color mixing, controllable intensity/brightness, and accurate/truthful rendering of colors. In preferred embodiments, the light source 606 comprises light emitting diodes (LEDs) with a high color rendering index (CRI). In preferred embodiments, the light source 606 comprises LEDs that generate light responsive to adjustments 218, 220, 222 for controlling light color/color temperature/color mixing, brightness/intensity, and/or other characteristics of light introduced from the light source box 216 and received by the light pipe 210 and supplied to the grip light 102 via the light pipe 180. In one embodiment, the LEDs comprise CREE XHP-35 High CRI type LEDs with approximately 10W output.

In other embodiments, the light source 606 may comprise a light source other than one or more LEDs, such as, for example, an incandescent light source, or high intensity discharge lamp, or laser illumination module, or other type of light source capable of projecting light through the light pipe 210, 180.

As previously mentioned, the light source box 216 may comprise circuitry for controlling the area light 202. In preferred embodiments, the light source box 216 includes circuitry for wirelessly controlling one or more work area lights 202.

Figure 7:
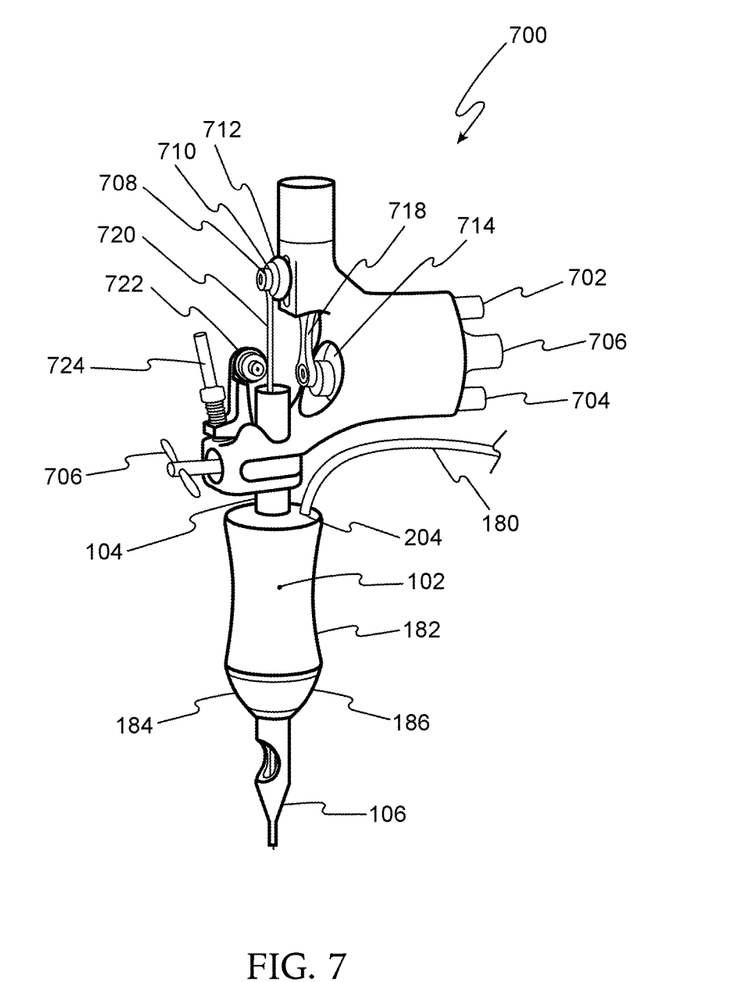
FIG. 7 is a perspective side view of a rotary type tattoo machine with the grip light shown in FIG. 2, according to preferred embodiments.

Illustrated in FIG. 7 is a perspective side view of a rotary type tattoo machine 700 with the grip light 102 shown in FIG. 2, according to preferred embodiments. The grip light 102 preferably comprises the attributes and features previously described in FIGS. 2-7 and with respect to the coil type tattoo machine 100 in FIG. 1. A clipcord is used to provide electrical power to negative 702 and positive 704 terminals, or, alternatively a power cable may be used with an RCA type connection 706. The rotary motor 714 spins the excenter 716, which moves the connecting rod 718 up and down. A needlebar pin holds a top hat type nipple 712, shown with the eye 710 of the needlebar 720 pushed onto the small (front) end 708 of the top hat nipple. The connecting rod 718 is coupled to the needlebar 720 via the needlebar pin. A needlebar retainer 722 is used to apply pressure against the needlebar 720, and a needlebar retainer screw 724 allows for adjusting the amount of pressure the needlebar retainer 722 provides. A tube vice screw 706 is used to tighten the tube vice clamp 726, which secures the grip light 102 to the rotary machine via tightening the clamp 726 about the outside surfaces of the tube 104.

The rotary type tattoo machine 700 is simpler, quieter, and has fewer exposed and serviceable components than typical coil type machines. Yet, as for the coil type machine 100 in FIG. 1, the tattooist still has several steps to setup the tattoo machine. The tattooist has to carefully attach the grip light 102 to the machine by inserting the tube 104 into the tube vice clamp (with the needlebar and eye already positioned within the tube 104), attach the needlebar eye to the top hat nipple, position the tube 104 within the tube vice for the desired needle protrusion 112 from the end of the tattoo tip, tighten the vice clamp, and adjust the needlebar retainer.

Figure 8:
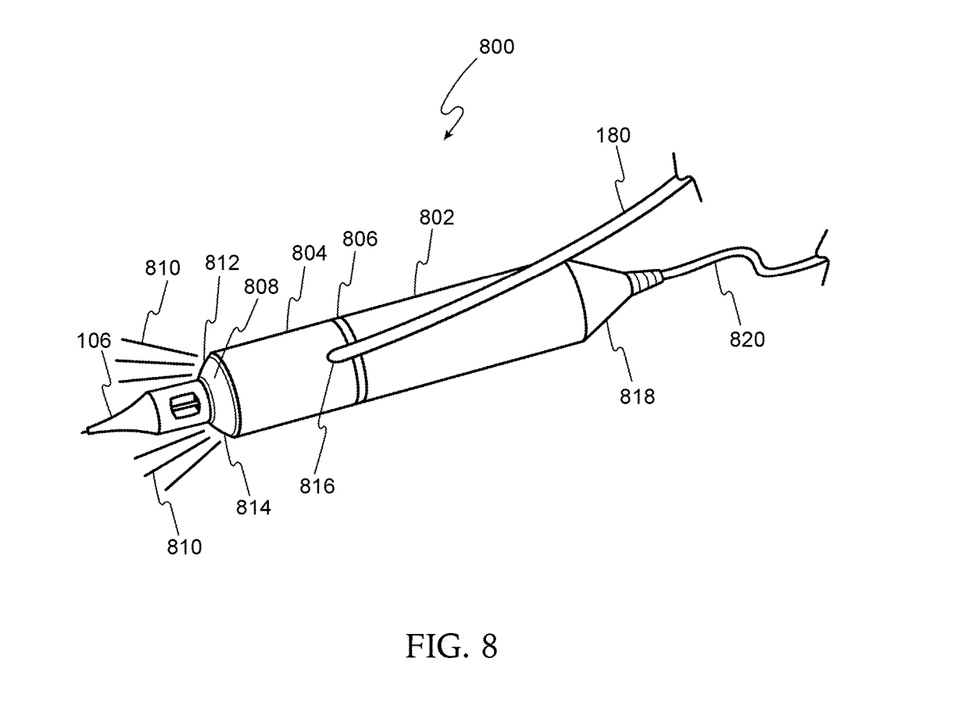
FIG. 8 is a side perspective view of a pen type tattoo machine with a grip light, according to preferred embodiments.

Pen shaped tattoo machines have been developed and provide improvements in terms of smaller size, quieter operation, fewer steps to setup, and fewer serviceable components. FIG. 8 is a side perspective view of a pen type tattoo machine 800 with a grip light 804, according to preferred embodiments. The rear housing 802 comprises a rotary motor, shown with a tapered end 818 opposite the tattoo tip 106 and connected to power via power cord 820. The rear housing 802 preferably threadably connects via a ring 806 to a grip light 804.

In preferred embodiments, the grip light 804 comprises a generally cylindrical grip having an inlet 816 for receiving a light pipe 180, light transmissive material 808 extending from the inserted end of the light pipe 180 to one or more outward surfaces 812, 814 from which light transmitted through the light transmissive material within the grip light 804 is projected 810 from the bottom or working end of the pen 800 to illuminate 810 the area proximate to the tattoo tip 106 and area being tattooed thereunder. The outward surfaces 812, 814 of the grip light 804 from which light is projected preferably comprises a 360 degree ring surrounding the tattoo tip 106.

In preferred embodiments, the portion of the pen 800 from the ring 806 to the tattoo tip 106 are substantially similar to the grip light 102 without tube 104 and using a threaded connection to secure the grip light 804 to the ring 806 and rear housing 802. The cross-section of the grip light 804 from the internal threads to the tattoo tip 106 are preferably substantially the same as in FIG. 3. The tattoo tip 106 preferably comprises a disposable needle cartridge as described in FIG. 5.

Disposable pen machine covers typically cover all but the tattoo tip 106, and are preferably stretched rearward to expose the (preferably clear optic material comprising) outward surfaces 812, 814 where transmitted light is projected from the grip light 804. Alternatively, disposable cover material is secured under tattoo grip tape applied to the barrel/grip portion of the grip light 804 so as to leave outward surfaces 812, 814 of the light transmissive material 808 exposed, and to cover the grip portion of the grip 804 and rearward over the rear housing 802, light pipe 180, and power cable 820.

Figure 9:
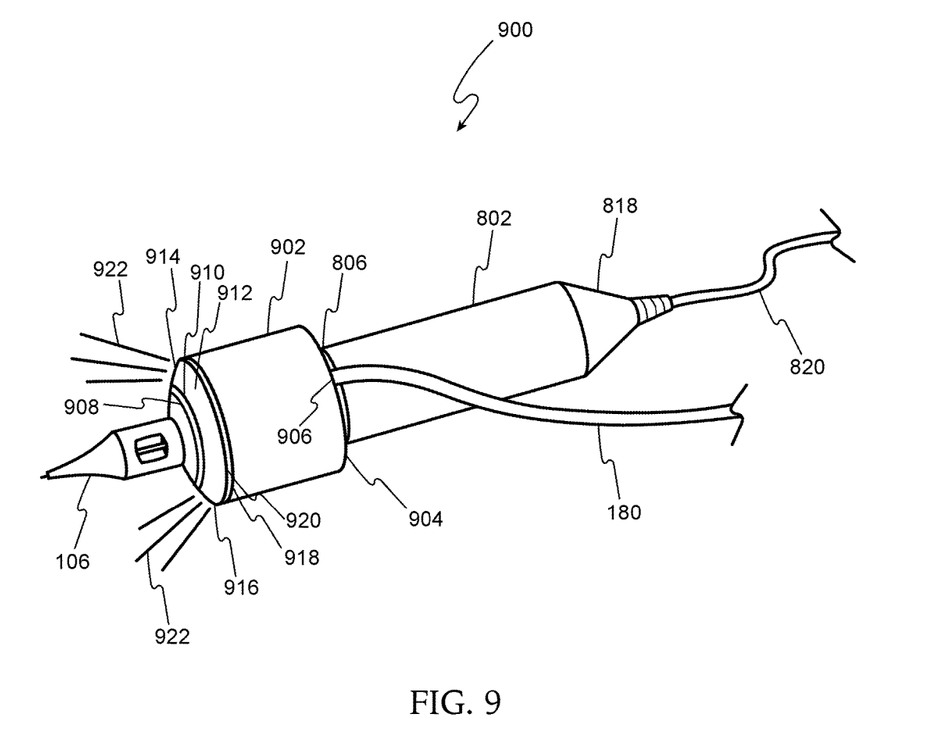
FIG. 9 is a side perspective view of a pen type tattoo machine with a grip light adapter, according to preferred embodiments.

FIG. 9 is a side perspective view of a pen type tattoo machine 900 with a grip light adapter 902, according to preferred embodiments. The grip light adapter 902 preferably threadably attaches over the grip portion of a pen type machine as in FIG. 8 that does not incorporate the inlet 816, light transmissive material 808, and outward surfaces 812, 814 included in grip light 804. Instead, in preferred embodiments and as shown in FIG. 9, the grip light adapter 902 slips over the grip end of the pen type machine and threadably attaches to ring 806. The grip light adapter 902 preferably includes an inlet 906 on a radial face/surface 904 for receiving a light pipe 180 and light transmissive material 912 extending from the inserted end of the light pipe 180 to one or more outward surfaces 914, 816 from which light transmitted through the light transmissive material within the grip light adapter 902 is projected 922 from the bottom or working end of the pen 900 to illuminate 922 the area proximate to the tattoo tip 106 and area being tattooed thereunder.

The grip light adapter 902 is preferably greater in diameter than the grip portion of the pen type machine to which the adapter is applied. As shown in FIG. 9, the grip light adapter 902 working end preferably comprises clear optic material from an inside diameter 910 to an outside diameter 920, and exterior grip surface material at an outside diameter 920. The pen type machine to which the grip light adapter 902 is applied, is illustrated in FIG. 9 with a constant diameter from the rear housing 802 extending forward to an edge 908 at the working end of the pen type machine. The outward surfaces 914, 916 of the grip light adapter 902 from which light is projected preferably comprises a 360 degree ring surrounding the tattoo tip 106.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A grip light for use with a tattoo machine comprising: an exterior grip surface extending from an upper grip portion downward toward a working end of said grip light and surrounding a longitudinal channel extending downward through said upper grip portion to said working end; light transmissive material surrounded by said exterior grip surface and extending from said upper grip portion downward from a light receiving surface to at least one bottom surface of said working end of said grip light; and an inlet adapted to receive light from a light pipe into said light receiving surface, permitting light from the light pipe to be projected from said working end of said grip light to illuminate an area proximate to said working end and an area therebelow.

2. The grip light of claim 1 wherein said longitudinal channel is sized and adapted to receive and secure a tattoo full tube, the full tube having a tube portion extending from said upper grip portion in a direction opposite said working end and a tattoo tip portion extending from said working end of said grip light when said full tube is secured within said longitudinal channel.

3. The grip light of claim 1 further comprising a tube extending from said upper grip portion in a direction opposite said working end, with said longitudinal channel extending through said tube.

4. The grip light of claim 3 wherein said grip light is autoclavable.

5. The grip light of claim 3 wherein said grip light is disposable.

6. The grip light of claim 1 wherein said working end of said grip light is sized and adapted to receive and secure a tattoo tip cartridge.

7. The grip light of claim 1 wherein said working end of said grip light is sized and adapted to receive and secure a tattoo needle cartridge.

8. The grip light of claim 1 wherein said light pipe is a light guide.

9. The grip light of claim 1 wherein said light pipe comprises at least one light guide optical fiber.

10. The grip light of claim 1 further comprising: a tube extending from said upper grip portion in a direction opposite said working end, with said longitudinal channel extending through said tube, said tube sized and adapted to be securely receivable by the tube vice clamp of a coil or rotary type tattoo machine.

11. The grip light of claim 1 further comprising a pen type tattoo machine securably fastened to and extending from said upper grip portion in a direction opposite said working end.

12. The grip light of claim 1 wherein said longitudinal channel of said grip light is sized and adapted to receive a grip portion of a pen type tattoo machine such that the grip light securably fits over said pen type machine grip portion.

13. The grip light of claim 1 further comprising a light source box having said light pipe extending therefrom, said light source box having a light source adapted to inject light into said light pipe, and said light pipe adapted to transmit light from said light source box to an end of said light pipe adapted to be received by said inlet of said grip light.

14. The grip light of claim 13 wherein said light source comprises one more light emitting diodes (LEDs).

15. The grip light of claim 13 wherein said light source box includes controls for controlling light color and intensity.

16. The grip light of claim 1 further comprising a work area light.

17. The grip light of claim 16 further comprising: a light source box having said light pipe extending therefrom, said light source box having a light source adapted to inject light into said light pipe, and said light pipe adapted to transmit light from said light source box to an end of said light pipe adapted to be received by said inlet of said grip light; and circuitry in said light source box adapted for control of said work area light.

18. The grip light of claim 1 wherein said bottom surface of said working end of said grip light comprises a ring-shaped surface that extends 360 degrees encircling said longitudinal channel or a tattoo tip extending from said working end of said grip, said ring-shaped surface permitting light from the light pipe to be projected from said working end of said grip light in a 360 degree pattern to illuminate said area proximate to said working end and said area therebelow.

19. The grip light of claim 18 wherein said grip light is autoclavable.

20. The grip light of claim 18 wherein said grip light is disposable.

* * * * *